(12) United States Patent
Chirdon et al.

(10) Patent No.: US 11,891,547 B2
(45) Date of Patent: Feb. 6, 2024

(54) PRODUCTION OF ADHESIVES AND OTHER GLUE-LIKE MATERIALS FROM UNEXTRACTED SEWAGE TREATMENT PLANT SLUDGES, ANIMAL MANURES AND ANIMAL MANURE-BASED SLUDGES, AND BACTERIAL/FUNGAL CELLS AND CELL COMPONENTS S AS DERIVED FROM CULTURING OPERATIONS

(71) Applicant: University of Louisiana at Lafayette, Lafayette, LA (US)

(72) Inventors: William Chirdon, Lafayette, LA (US); Mark Zappi, Lafayette, LA (US); Rafael Hernandez, Lafayette, LA (US); Chelsea Trahan, Lafayette, LA (US)

(73) Assignee: University of Louisiana at Lafayette, Lafayette, LA (US)

( * ) Notice: Subject to any disclaimer, the term of this patent is extended or adjusted under 35 U.S.C. 154(b) by 9 days.

(21) Appl. No.: 17/205,081

(22) Filed: Mar. 18, 2021

(65) Prior Publication Data

US 2021/0253921 A1    Aug. 19, 2021

Related U.S. Application Data

(63) Continuation-in-part of application No. 16/564,560, filed on Sep. 9, 2019, now abandoned.

(60) Provisional application No. 62/730,615, filed on Sep. 13, 2018.

(51) Int. Cl.
| | | |
|---|---|---|
| C09J 189/00 | (2006.01) |
| C09J 189/04 | (2006.01) |
| C07K 1/14 | (2006.01) |
| C02F 11/18 | (2006.01) |

(52) U.S. Cl.
CPC ............... *C09J 189/04* (2013.01); *C07K 1/14* (2013.01); *C02F 11/18* (2013.01)

(58) Field of Classification Search
None
See application file for complete search history.

(56) References Cited

U.S. PATENT DOCUMENTS

| | | | |
|---|---|---|---|
| 6,752,848 B2 * | 6/2004 | Logan ...................... | C05D 3/02 71/14 |
| 2004/0115090 A1 * | 6/2004 | Andersson .............. | C05F 17/00 422/38 |
| 2014/0261075 A1 * | 9/2014 | Chirdon ................. | C09J 189/04 435/134 |
| 2016/0073671 A1 * | 3/2016 | Geistlinger ............. | A23L 27/26 426/61 |

* cited by examiner

*Primary Examiner* — Stefanie J Cohen
(74) *Attorney, Agent, or Firm* — Kean Miller LLP; Lauren J. Rucinski; Brian J. Servé

(57) ABSTRACT

A system and method for treatment of biomass originating from wastewater treatment biosolids to obtain valuable adhesives and composite materials is described herein. Some embodiments do not require purification of a biomass product or residue to produce an adhesive.

11 Claims, 4 Drawing Sheets

Method Descriptions:
A    10 g wet biosold, 27 mL water, 3 mL 10 M NaOH
B    10 g wet biosolid, 6 mL water, 1.6 g 1M citric acid, biosolid frozen with water added before use
C    10 g wet biosolid, 3 mL 10M NaOH, kept @ 50C
D    6 g dried, ground biosolid, 4 g water, 3 mL 10 M NaOH, kept at 50°C

PRODUCTION OF ADHESIVES AND OTHER GLUE-LIKE MATERIALS FROM UNEXTRACTED SEWAGE TREATMENT PLANT SLUDGES, ANIMAL MANURES AND ANIMAL MANURE-BASED SLUDGES, AND BACTERIAL/FUNGAL CELLS AND CELL COMPONENTS S AS DERIVED FROM CULTURING OPERATIONS

CROSS REFERENCE TO RELATED APPLICATIONS

This application is a Continuation in Part of U.S. patent application Ser. No. 16/564,560 titled "PRODUCTION OF ADHESIVES AND OTHER GLUE-LIKE MATERIALS FROM SEWAGE TREATMENT PLANT SLUDGES, ANIMAL MANURES AND ANIMAL MANURE-BASED SLUDGES, AND BACTERIAL/FUNGAL CELLS AND CELL COMPONENTS S DERIVED FROM CULTURING OPERATIONS" filed Sep. 6, 2019, now abandoned, which claims priority to U.S. Provisional Application No. 62/730,615 titled "PRODUCTION OF ADHESIVES AND OTHER GLUE-LIKE MATERIALS FROM SEWAGE TREATMENT PLANT SLUDGES, ANIMAL MANURES AND ANIMAL MANURE-BASED SLUDGES, AND BACTERIAL/FUNGAL CELLS AND CELL COMPONENTS S DERIVED FROM CULTURING OPERATIONS", filed on Sep. 13, 2018.

STATEMENT REGARDING FEDERALLY SPONSORED RESEARCH OR DEVELOPMENT

Not Applicable.

REFERENCE TO A "SEQUENCE LISTING," A TABLE, OR A COMPUTER PROGRAM

Not Applicable.

FIELD OF THE INVENTION

Figure 1:
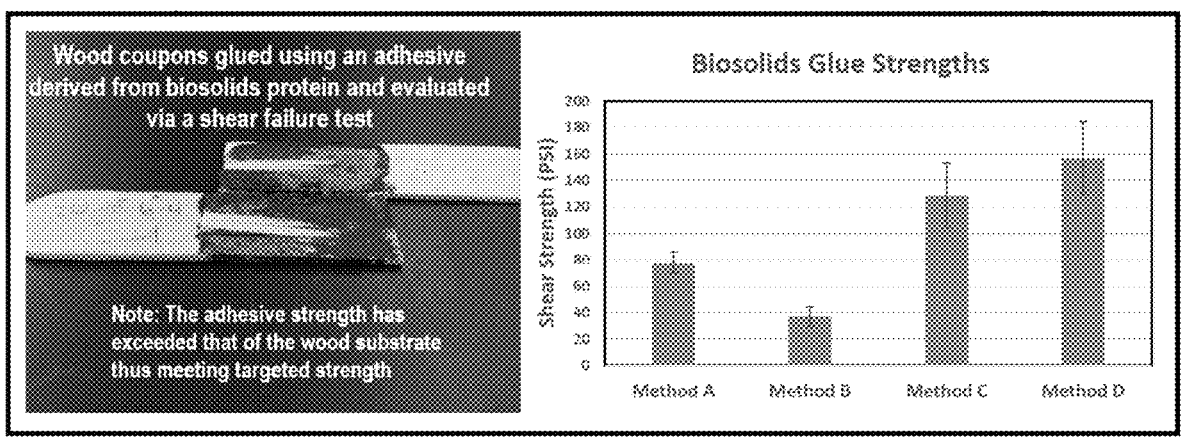
FIG. 1 illustrates the shear strength of several example formulations of adhesive production.

The present invention relates generally to the manufacture of adhesives, especially as it relates to materials that may be utilized to manufacture adhesives. The invention relates to organic material typically considered waste as sources of feedstock to manufacture adhesives. In particular, the invention relates to sludges generated at wastewater treatment plants (WWTP), manures, and other bacterial and fungal sources that have the potential to be used as feedstock to manufacture protein-based adhesives.

BACKGROUND OF THE INVENTION

Waste generated from wastewater treatment operations include primary sludge, secondary sludge, and biosolids. Primary sludge is produced through initial settling or capture of solid or semi-solid materials including manure. Secondary sludge includes biomass produced in an aerobic or anaerobic biological WWTP process. Biosolids are generated after some degree of biodegradation of primary and secondary sludge often followed by dewatering. All of these sludges from WWTPs contain some amount of protein.

The sludge wastes derived from the activated sludge process are composed mainly of bacteria and fungi that are wasted to maintain targeted bioreactor microbial populations (aka. waste activated sludge or WAS). The WAS is often reduced in terms of mass through the biological process of digestion, both anaerobic and aerobic systems are used. The resulting wet, organic-rich waste stream generated after digestion and dewatering is referred to as "biosolids." Anaerobic digestion is used at hundreds of US WWTP facilities which allows for the production of biogas which is becoming an increasingly important biofuel. Typical solids content of biosolids are in the 15% to 40% w/w range (USEPA, 1999).

The amount of biosolids produced in the US requiring disposal exceeds 7,000,000 dry tons per year (USEPA, 1999; Kinney, et al., 2006). These mainly microbial-based wastes generally contain 20-80% protein (generally around 60%), 10-40% carbohydrates (generally around 30%), and 0-15% lipids (generally around 5%) (Dufreche, et al., 2007; Westgate and Park, 2010; Pervaiz and Sain, 2011). The fertilizer value of biosolids is minimum because of low N:P:K values in the 5:3:0.5 range (Jacobs and McCreary, 2001) which yields a calculated fertilizer value of biosolids at around $30/dton. About 70% of the biosolids generated at US wastewater treatment plants are either land-applied as a natural fertilizer or landfilled, both having disposal costs in the $30 to $100/dton (dry ton) range (Mitchell, 2009; North East Biosolids & Residuals Association, 2011; Moss, et al., 2013). The national average appears to be around $40-$50/dton. Albeit, some commercialization attempts have been made to package biosolids as an "organic" fertilizer, minimal market success has been established. Thus, biosolids generally remain a wet waste stream that requires payment for disposal because of the lack of a viable commercial use.

WAS has really never been considered a feedstock nor an end product for any commercial process. It is thickened from 4 g/l solids to ~1%-5% solids prior to feeding into a digester. It is routinely "digested" using aerobic or anaerobic digestion and thus is an intermediate sludge produced within WWTPs. The protein structures of the aerobic microbes will be slightly different from the anaerobes (Zhang, et al., 2015) which may offer an advantage (or not).

Concentrated animal feeding operations (CAFOs) produced large quantities of biological-based waste, via manures, requiring disposal. Examples include manures from poultry, dairy, and swine raising operations. In all of these cases, digestive feces and undigested feed are the primary constituents resulting in the chemical compositions being high in lignocellulosics (30-50%), protein (18-50% w/w), carbohydrates (20-50%), lipids (5-10%), and gut bacteria (<10%). These manures are also relatively low in fertilizer value with N:P:K values generally less than 3:2:1. Of the protein ranges shown, cattle/dairy manures tend to have lower protein levels with poultry having the highest. Typically, dairy and swine wastes are treated using anaerobic lagoons or digesters (Lim, et al., 2003; Riano and Garcia-Gonzalez, 2014). Poultry litter is most often disposed onto open forage fields as fertilizer and/or used as a feed supplement to cattle feeding operations (Kelleher, et al., 2002; Daniel and Olson, 2005; Ritz, et al., 2017). It has a protein content in the 20-40% (w/w) range.

Proteins have long been used to make quality adhesives of commercial value (Frihart, 2015). Most of these proteins have come from either agricultural crops (e.g., soyor corn) or animal residuals (blood and rendered animal parts). Proteins are the biochemical building blocks of most living organisms. They are essentially linear polypeptides made up of amino acids which contain amino groups (—NH2) and carboxylic groups (—COOH). There are only 20 or so amino acids that can make up the proteins in all living systems, including those in WAS and biosolids. The basic structural categories of proteins are fibrous and globular shapes configured as strands or folds, respectively. Protein-based adhesives were the industry standard until the 1960s when petroleum-based products began to take over the market (Khosravi, 2011; Frihart, 2015).

DETAILED DESCRIPTION

Described herein is a composition and method for the creation of adhesives from unextracted proteins within the chemical matrices of wastewater treatment plant sludges, manures, waste bacterial and fungal cells, and cultured bacteria and fungi. In many cases, these feedstocks can be processed into adhesives, including glues, binders, resins, and caulks, without any water addition or removal or delipification (removal of lipids). The optimal solids content (W/W) falls within the range of 15 to 60% range. However water may be added or removed using dewatering methods to achieve target levels. The adhesives are produced using a heated, alkaline-based process that denatures the proteins into adhesives.

Other sources of protein-containing waste that could be used to produce adhesives include industrial waste streams (e.g. "distillers grain") that are high in bacterial fungal cells along with fermentation broth constituents. Examples include distillers grain, pharmaceutical sludges, and enzyme production systems. Other sources include cultured microorganisms (e.g., bacteria and fungi) fed with carbon sources such as aliphatic gases (methane, propane, etc.), carbohydrates (sugars, starches, etc), and other cheap carbon sources (waste food, yard clippings, etc). A good example would be methanotrophs which are aerobic, heterotrophic bacteria that utilize methane (via natural gas, for example) as a carbon source. Microbial proteins can also be produced from genetically engineered organisms like E coli, fungi, and oleaginous heterotrophs.

Chemical matrices of the biotreatment solids (WAS and biosolids) and other microbial/manure-based systems (DDG, poultry litter, etc.) can be more heterogeneous and complex (particularly WAS and biosolids) than that of plant systems (soy and corn). This is also true for cultured microbes via industrial processes or culturing simply for microbial growth. These chemical matrices may poise challenges to the processing of these proteins compared to cleaner chemical matrices. Thus, a series of preliminary experiments were initiated to evaluate if the more complex chemical matrix of wet biosolids can be used to produce an adhesive of commercial value using neat proteins from biosolids without dewatering, purification, or formaldehyde addition. FIG. 1 summarizes the results from this effort (the different formulations shown varied by %-solids with the better forming range being 20% to 50%). Note that the adhesive produced exceeded the strength of the wood indicating a product of great potential. And, for every pound of wet biosolids used, one pound of this adhesive was produced! No dewatering or solids modification appears necessary. However, if a purer form of protein is wanted, the cells or manures from any of the listed feedstocks are easily dewatered at a fairly low cost, the proteins extracted and purified, and the purified proteins also can be used in adhesive production. Both options are part of this disclosed invention.

Some other benefits to the process are recognized. The WAS and biosolids are produced as either 0.5-5% or 18-30% (w/w) solids, respectively, with balance being water (WWTP effluent). Microbial cells are often dewatered (or can be) to similar solids concentrations within other fermentation systems (ex. methanotrophs). Embodiments of the process can operate at 10%-70% solids ideally making further dewatering of the feedstocks likely unnecessary. In some embodiments of the invention, WAS, manures, and some microbial biomasses may need additional dewatering. If WWTP sludges are used, these dewatering facilities are likely already at WTTPs. If a WWTP sludge has been dewatered to greater than ~40% solids, then make-up water is readily available by reintroducing the WWTP effluent back into the sludge (this is a free water source that will not impact potable water resources). If the other feedstocks need more water, then water from WWTP (effluent) or other source of water can be used to reduce the solids concentration via simple water addition and mixing (agitated via mixers and/or recycle pumps).

Based on our recent data on biosolids, the process produces a very low amount of waste residuals with only an estimated maximum of 5% of input mass are not incorporated into the adhesive formulation. These residuals are mainly floating fixed solids, but very little has been produced in past runs. If protein purification or other forms of pretreatment or process amendments are used, then more waste products may be produced.

Figure 2:
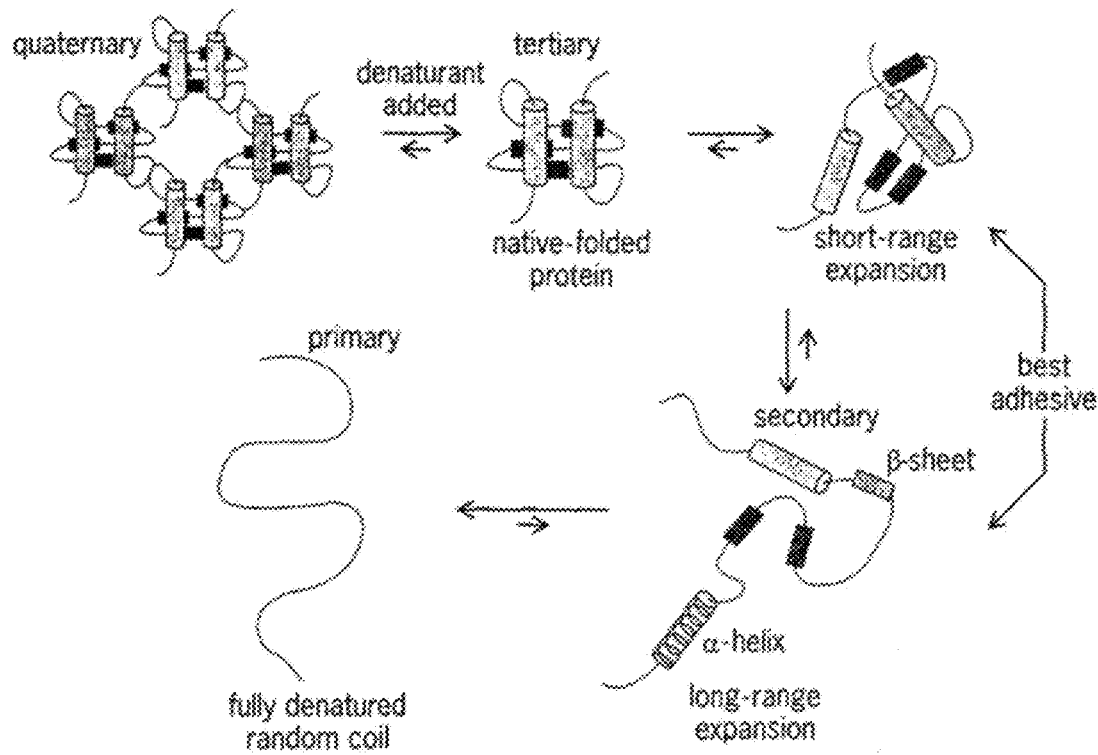
FIG. 2 illustrates the stepwise denaturing of proteins to form adhesives.

The overall mechanism for production of the adhesives is a protein denaturing process that involves an aqueous reaction matrix. The goal of the denaturation process for the formation of adhesives is to dissolve the quaternary and tertiary structures of the protein (and perhaps partially, the secondary), effectively converting the proteins into structures resembling polymeric random coils once they have unfolded. FIG. 2 illustrates protein unfolding as it is postulated to occur in our invention during processing. The addition of a strong base increases the pH of the proteins above their isoelectric point. Under this condition, the ions in the solution interfere with the hydrogen bonds and the electrostatic dipole-dipole interactions which allows the proteins to retain their shape and higher order structures. Many of the natural, covalent crosslinking groups (including cysteine and disulfide bonds) in these proteins are also vulnerable to disassociation under alkaline conditions. This process also exposes the hydrophilic portions of proteins, which allows these adhesive groups to adsorb to substrates or fillers; hence, an adhesive is produced. While these processing steps/mechanisms have long been used to produce adhesives from proteins from plants (soy, corn, wheat, etc.), animals (blood, milk, meat, etc.), our invention takes the same general processing methods and applies it to the never-considered feedstock of manures and bacterial/fungal waste/cultured materials.

Proteins within the invented feedstocks for the invention are denatured via an optimized water-based process with engineered, controlled system operational parameters of reaction time, temperature, mixing, heat ramping, chemical dose rates, and pH. Depending on the other parameters, typical reaction time may range from a few seconds to over 3 hours, temperature may range from 0° C. to 120° C., and pH adjustment from 10 to 14. Optimized conditions are more typically expected to be between 45-70 minutes, 50° C.-60° C. with a pH between 11-12. The denaturant solution may also be acidic.

This processing converts the proteins into an adhesive state to form commercial adhesives. One of the key challenges in creating adhesives from natural proteins through denaturation is that the reactants, temperatures, and conditions that are used to denature proteins typically have the undesirable effect of hydrolyzing the protein chains into smaller fragments which produces a lower quality product. This problem is typically addressed by the careful control of the denaturation conditions, which requires an understanding of the underlying kinetics. The denaturation process dissolves the quaternary and tertiary structures of the protein (see FIG. 2), converting the proteins into structures resembling polymeric random coils. This process also exposes the hydrophilic portions of proteins, which allows these adhesive groups to adsorb strongly to substrates and filler materials. However, the conditions the invented process uses to denature proteins, especially temperature and pH modification, also hydrolyze the proteins. This results in lower molecular weight protein fragments that suffer a significant loss of tensile strength, especially when the chains become too short to entangle with each other. Fortunately, there is typically a process window that we invented where the reaction time, temperature, and pH can be controlled so as to achieve extensive denaturation without significant hydrolysis. Therefore, if the kinetics of hydrolysis and denaturation can be quantified, the adhesive properties can be optimized. An optimized process condition that has proved effective involved a 40% solids concentration of bacterial cells (biosolids) mixed at a pH of 11 at 40° C. Sodium hydroxide is used to increase the pH to this level but lime has also been proven to be effective (any strong base will suffice). Other bases, such as potassium hydroxide, may also serve this purpose. Mixing for 90 minutes at the maintained temperature and pH yields a good quality adhesive without protein extraction or purification.

Findings of research disclosed herein reveal a process for making adhesives from various biomasses without extraction of the proteins. This finding is of significance as less waste is produced, materials that would become waste are incorporated into the adhesive. It is expected that cost savings and economic benefits would be obtained.

Figure 3:
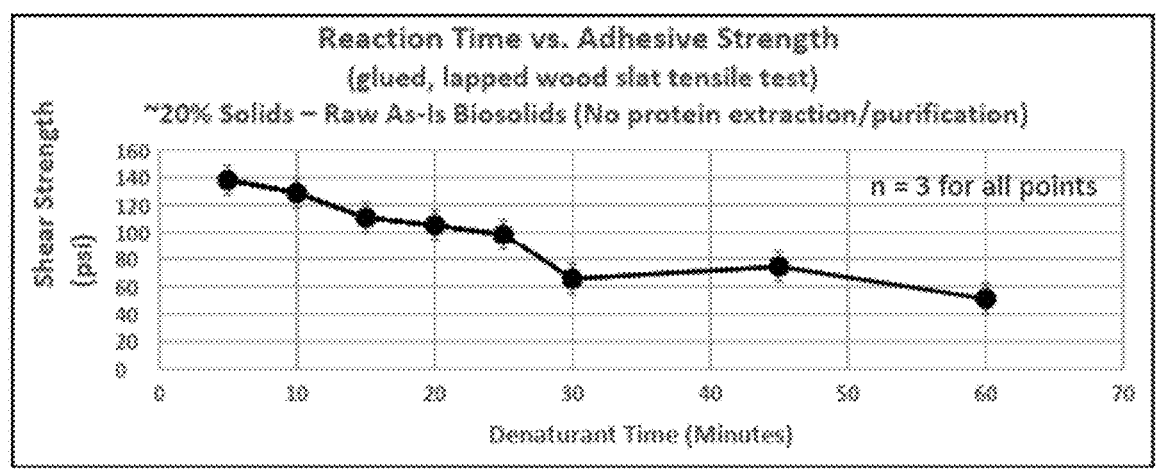
FIG. 3 illustrates the relationship between reaction time and adhesive strength.
Figure 4:
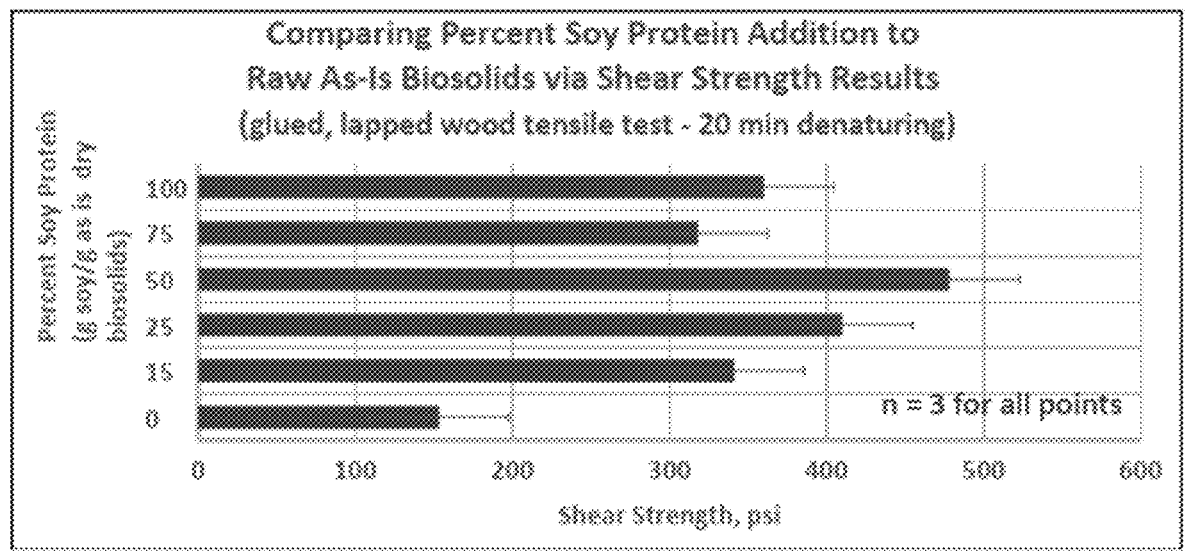
FIG. 4 illustrates the effect of addition of soy protein.

Results (see FIG. 3) have shown that the adhesive strength decreases as the reaction time increases past 5 minutes. Accordingly, an advantage is seen where adhesives are made from biosolids with reaction times of less than 30 minutes, preferably less than 20 minutes and most preferably less than 10 minutes. Shortening the reaction time below 5 minutes may also be beneficial for the adhesive strength if the observed trend continues and may also improve the long-term adhesive strength. Reaction times as low as a few seconds to mix the components may be desirable. The rate of the reaction from recent testing can achieve appreciable strength gain as rapid as 30 second but strength gain optimal in the 5 minute range Whereas adhesives made from purified plant protein (i.e., soy) have a higher adhesive strength compared to adhesives made from biosolids, as shown in FIG. 4, adhesives made from a mixture of purified plant protein and biosolids have adhesive strengths greater than that from the purified plant protein. Specifically, adhesives made with mixtures containing 25-50% soy protein (or extrapolating between examples, 20-62.5%) showed adhesive strengths greater than adhesives made from either pure soy protein or pure biosolids.

Figure 5:
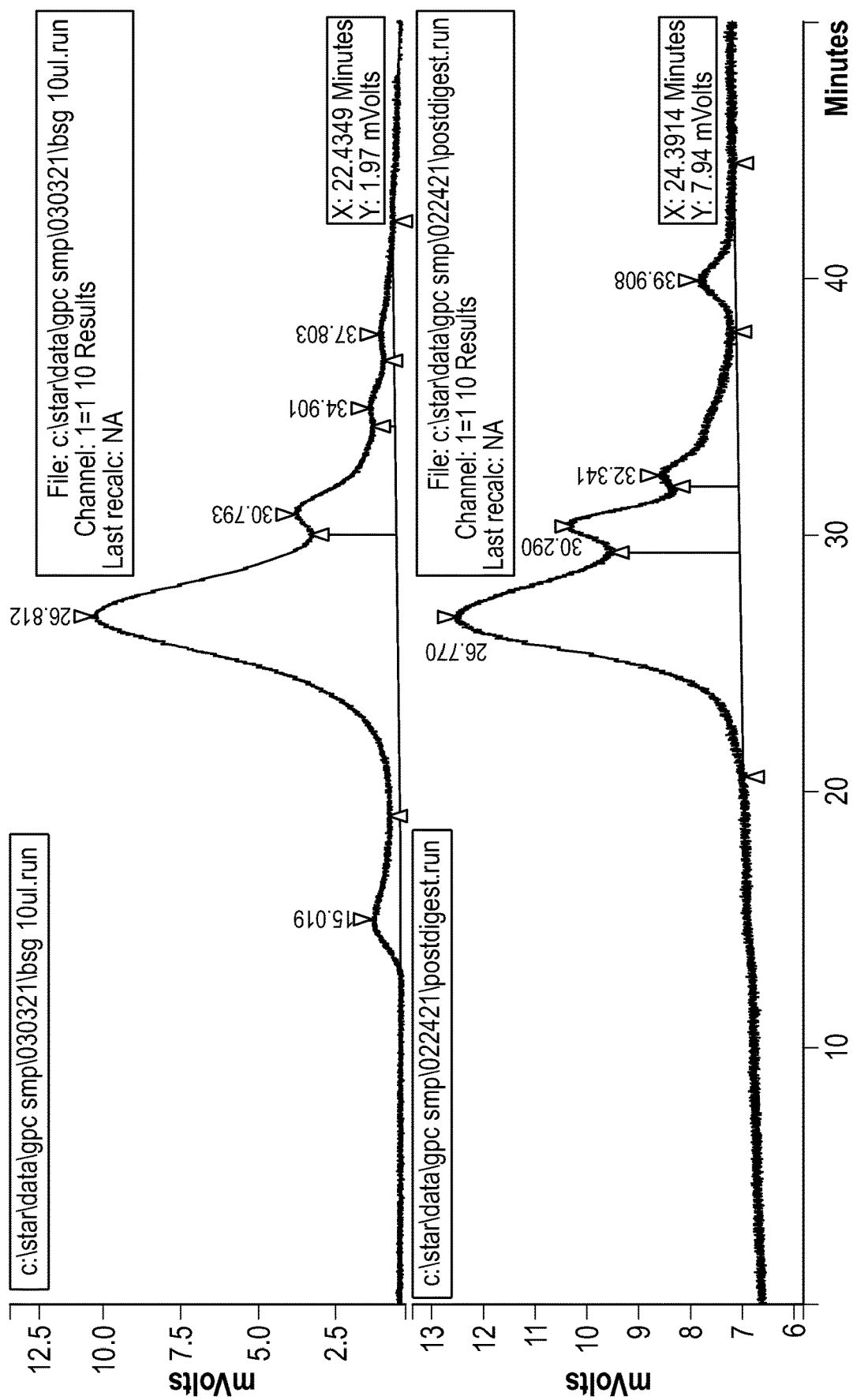
FIG. 5 discloses chromatographs of denatured biosolids.

Unexpected results from Gel Permeation Chromatography (GPC) experiments as shown in FIG. 5 were obtained. The line in the top graph of FIG. 5 represents the chromatogram for the denatured biosolids. The line from the bottom graph shows the results for the sludge without denaturing. The denaturant adds a peak at roughly 15 minutes, which indicates the formation of a higher molecular weight (MW) structure (shorter residence times indicates higher MW). From the previous work, and "conventional wisdom" with glues, the denaturant (NaOH) is thought to denature the proteins (dissolving higher level structures) while at the same time hydrolyzing the proteins (destroying the primary structure). Accordingly, the typical goal in making glue is to control process conditions to allow for denaturation while controlling reaction time (or minimizing aggressive reaction conditions) to minimize hydrolysis and molecular weight degradation. GPC results have shown that after the denaturant is added the molecular weights of the proteins increase from 19,500 daltons to 643,000 daltons. If the chains are hydrolyzing, we would expect the MW to decrease. Accordingly, this is evidence that the proteins are combining to form larger molecules with superior adhesive properties. Thus, with larger molecules forming, this provides evidence of complexation of the proteins into larger adhesive linked polymers which in turn verifies the chemical and physical conversion of the biomass materials into a new chemical form as an adhesive.

The process can be enhanced through the following methods: delipification (removing the lipids); sonication (irradiation with ultrasound); high shear mixing; chemical oxidation; and protein extraction/purification. Embodiments of the invention include these methods as they are effective for protein conversion into adhesive. Details of each potential enhancement are listed below:

Even though lipids did not adversely impact the synthesis of adhesives using the dilipified microalgae cake (<2% lipid residuals) from our past R&D activities, biosolids and WAS could contain as much as 15% lipids (although most of these sludges have lipid contents <5%). Lipids will hydrolyze then methylate or saponify in the presence of hydroxide producing free fatty acids and surfactants which are not considered beneficial reactions to the proposed process. The impacts of these non-targeted products of reaction on the performance of adhesives will be monitored by tracking their formation during the reaction. These products of reaction may act as partial scavengers of the hydroxide, minimizing protein hydrolysis, and thus, reducing adhesive performance.

The impact of ultrasound on conditioning the feedstocks/sludges prior to adhesive processing can enhance the process. Ultrasound is commonly applied to lyse cells prior to protein extraction from bacteria. The application of this technology could enhance reaction kinetics by making the proteins more accessible to the sodium hydroxide and conditioning the protein fragments into accelerated reactions.

The use of high shear mixing enhanced the invented process through improved protein access to the process reagents. Bleakley and Hayes (2017) report that laboratory blender experiments significantly enhanced protein access for digestibility and direct extraction which indicates that it exposes the proteins for easier chemical reaction (in our case, accelerated and more complete denaturing). Thus, we find that this increased reactive state also applies to our invented adhesive process.

The use of ozone, peroxone, hydrogen peroxide, or Fenton's Reagent for partial oxidation of the cell structures within the sludges will be evaluated with hopes that both cell rupture and partial oxidation of the proteins will enhance the rate and extent of protein denaturing. The oxidation of bacterial cells and proteins contained within the cells have been found to enhance the reactivity of proteins toward other chemical reactions (Parrado, et al., 2003; Bougrier, et al., 2007). A sparged reactor is used to dose the ozone. Hydrogen peroxide ($H_2O_2$) alone can be added to initiate peroxone reactions at hydrogen peroxide levels up to 1,000 mg/l. Hydrogen peroxide iron salts can be added to accelerate targeted benefits at concentrations ranging from 100 mg/l to 10 g/l with iron added at a $H_2O_2$:Fe ratio ranging from 10:1 to 100:1.

Eliminating sludge matrix effects by capturing the proteins from the feedstocks thereby allowing them to react as a purer form of protein can improve the reactions and resulting product characteristics. An aqueous alkaline/acid separation procedure followed by gravimetric separation is performed as described by others (Pervaiz and Sain, 2011). With this process, the proteins are solubilized via base addition (pH to 12), followed by sonic cell rupture, than acidification (sulfuric) of the proteins into an insoluble form. Note that protein harvesting from similar systems been found to be technically and reportedly economically feasible for single-cell protein from CH4 feeds (methanotrophs) and ammonia feeds within ammonia oxidizing activated sludge systems.

Protein-based adhesives typically have poor water resistance to wetting unless coated with a waterproof resin (which is claimed as part of this disclosure). Several methods have been successfully used to greatly improve the water resistance of protein adhesives. Various amendments to the processing of proteins to form adhesives with both improved water resistance and strength include the additions of ethylene glycol, lignin, tannins, polyamidoamine-epichlorohydrin (PAE) resin, sodium bisulfate (NaHSO3), sodium dodecyl sulfate (SDS) surfactant, lignin amine, and calcium carbonate—all as part of the invention.

The invention claimed is:

1. A method for producing an adhesive from biomass, comprising the steps of: a. obtaining a biomass; b. denaturing proteins in said biomass to generate an adhesive product without requiring any prior extractions; c. wherein the denaturing step is a heated, alkaline-based process while under high shear; d. wherein the adhesive product has a shear strength of greater than 350 psi.

2. The method of claim 1, wherein the denaturing step occurs between 0° C. and 120° C. with a reaction time of between 30 seconds to 120 minutes.

3. The method of claim 1, wherein the denaturing step occurs between 15° C. and 70° C. with a reaction time of between 30 seconds to 20 minutes.

4. The method of claim 1, wherein the denaturing step occurs between 50° C. and 60° C. with a reaction time of between 30 seconds to 20 minutes.

5. The method of claim 1, wherein the denaturing step occurs between 70° C. and 120° C. with a reaction time of between 30 seconds to 20 minutes.

6. The method of claim 2, wherein the biomass comprised wastewater treatment sludge selected from the group consisting of primary sludge, secondary sludge; and biosolids.

7. The method of claim 2, wherein the biomass comprises cultured microorganisms.

8. The method of claim 2, wherein the biomass comprises animal-based manures.

9. The method of claim 2, wherein a purified protein is mixed with the biomass prior to denaturing.

10. The method of claim 1, wherein the adhesive product comprises 20-62.5% of the denatured proteins.

11. A method for producing an adhesive, comprising the steps of: a. mixing from 20-62.5% purified plant protein with 37.5%-80% biomass obtained from a waste source forming a biomass and protein mixture; b. denaturing said biomass and protein mixture without any prior extractions in a heated, alkaline-based process while under high shear with a reaction time of between 30 seconds to 20 minutes to form an adhesive with a shear strength of greater than 350 psi and a molecular weight greater than 50,000 daltons; wherein the biomass obtained from a waste source comprised wastewater treatment sludge selected from the group consisting of primary sludge, secondary sludge, and biosolids.

* * * * *